(12) United States Patent
McAllister

(10) Patent No.: US 8,454,992 B2
(45) Date of Patent: Jun. 4, 2013

(54) PANELED CAPSULE SHELLS FOR RELEASE OF PHARMACEUTICAL COMPOSITIONS

(75) Inventor: Stephen Mark McAllister, Sandwich (GB)

(73) Assignee: Capsugel Belgium NV, Bornem (BE)

( * ) Notice: Subject to any disclaimer, the term of this patent is extended or adjusted under 35 U.S.C. 154(b) by 388 days.

(21) Appl. No.: 12/285,843

(22) Filed: Oct. 15, 2008

(65) Prior Publication Data

US 2009/0110721 A1 Apr. 30, 2009

Related U.S. Application Data

(60) Provisional application No. 60/960,787, filed on Oct. 15, 2007.

(51) Int. Cl.
*A61K 9/48* (2006.01)

(52) U.S. Cl.
USPC ........... 424/451; 424/454; 424/457; 424/462; 264/299; 264/328.1

(58) Field of Classification Search
None
See application file for complete search history.

(56) References Cited

U.S. PATENT DOCUMENTS

| | | |
|---|---|---|
| D33,284 S | 10/1900 | Clement |
| 691,687 A | 1/1902 | Wilson |
| 1,079,438 A | 11/1913 | Pollock |
| 2,718,980 A | 9/1955 | Strom |
| 3,048,526 A | 8/1962 | Boswell |
| 3,186,910 A | 6/1965 | Glassman |
| 3,228,789 A | 1/1966 | Glassman |
| 3,823,816 A | 7/1974 | Controulis et al. |
| 4,196,565 A | 4/1980 | Bodenmann et al. |
| 4,442,941 A | 4/1984 | Keith |
| 4,487,327 A | 12/1984 | Grayson |
| 4,543,138 A | 9/1985 | Bollinger et al. |
| 4,564,363 A | 1/1986 | Bagnall et al. |
| 4,576,284 A | 3/1986 | Wittwer et al. |
| 4,591,475 A | 5/1986 | Tomka et al. |
| D285,837 S | 9/1986 | Wittwer |
| 4,655,840 A | 4/1987 | Wittwer et al. |
| 4,678,516 A | 7/1987 | Alderman et al. |
| 4,724,019 A | 2/1988 | Brown et al. |
| 4,738,724 A | 4/1988 | Wittwer et al. |
| 4,738,817 A * | 4/1988 | Wittwer et al. .......... 264/328.14 |
| 4,764,378 A | 8/1988 | Keith et al. |
| 4,774,092 A | 9/1988 | Hamilton |
| 4,790,881 A | 12/1988 | Wittwer et al. |
| 4,792,451 A | 12/1988 | Kim |
| 4,793,493 A | 12/1988 | Makiej, Jr. |
| 4,806,337 A | 2/1989 | Snipes et al. |
| 4,893,721 A | 1/1990 | Bodenmann et al. |
| 4,899,516 A | 2/1990 | Krieger et al. |
| 4,915,954 A | 4/1990 | Ayer et al. |
| 4,936,461 A | 6/1990 | Makiej, Jr. |
| 4,964,262 A | 10/1990 | Moser et al. |
| 5,004,601 A | 4/1991 | Snipes |
| 5,074,426 A | 12/1991 | Goodhart et al. |
| 5,082,655 A | 1/1992 | Snipes et al. |
| 5,135,752 A | 8/1992 | Snipes |
| 5,139,790 A | 8/1992 | Snipes |
| 5,223,265 A | 6/1993 | Wong |
| 5,244,668 A | 9/1993 | Snipes |
| 5,312,008 A | 5/1994 | Davis |
| 5,312,388 A | 5/1994 | Wong et al. |
| 5,312,390 A | 5/1994 | Wong |
| 5,443,461 A | 8/1995 | Atkinson et al. |
| 5,456,919 A | 10/1995 | Patell et al. |
| 5,672,359 A | 9/1997 | Digenis et al. |
| 5,750,143 A | 5/1998 | Rashid et al. |
| 5,769,267 A | 6/1998 | Duynslager et al. |
| 5,871,116 A | 2/1999 | Picchietti |
| 6,200,600 B1 | 3/2001 | Rashid |
| 6,367,228 B1 | 4/2002 | Wurst et al. |
| D481,456 S | 10/2003 | McAllister et al. |
| D493,518 S | 7/2004 | McAllister et al. |
| D501,549 S | 2/2005 | McAllister et al. |

(Continued)

FOREIGN PATENT DOCUMENTS

| | | |
|---|---|---|
| AU | 2005248930 | 1/2006 |
| BE | 900950 | 4/1985 |

(Continued)

OTHER PUBLICATIONS

G. Cuff et al. "A Preliminary Evaluation of Injection Molding as a Technology to Produce Tablets," Pharmaceutical Technology, vol. 22, No. 6, Jun. 1998.

(Continued)

*Primary Examiner* — Hasan Ahmed
(74) *Attorney, Agent, or Firm* — Finnegan, Henderson, Farabow, Garrett & Dunner, LLP

(57) ABSTRACT

Capsule shells for use in multi-part dosage forms have generally cylindrical shell members with a snap fit component on an interior surface adjacent an open end, for connection to a linker part of the dosage form. The shell member also has a plurality of spaced apart integrally formed thin (relative to circumferentially adjacent shell member portions) panels located adjacent a closed shell member end, for preferential dissolution and release of pharmaceutical compositions from the shell member interior. The ratio of the thickness of the panels to the thickness of the shell member ranges from about 0.2 to about 0.6. The panels can be integrally formed together with the shell member as reliefs or depressions on the inner surface of the shell member by injection molding, and panel thicknesses as thin as about 0.1 mm can be achieved.

30 Claims, 3 Drawing Sheets

U.S. PATENT DOCUMENTS

| | | | |
|---|---|---|---|
| D501,550 S | 2/2005 | McAllister et al. | |
| D506,545 S | 6/2005 | McAllister et al. | |
| 6,929,803 B2 | 8/2005 | Wong et al. | |
| D516,714 S | 3/2006 | McAllister et al. | |
| 7,163,693 B1 | 1/2007 | Clarke et al. | |
| 2001/0008637 A1 | 7/2001 | Hochrainer et al. | |
| 2003/0029558 A1 | 2/2003 | Hochrainer et al. | |
| 2003/0049311 A1* | 3/2003 | McAllister et al. | 424/452 |
| 2003/0068369 A1 | 4/2003 | McAllister et al. | |
| 2003/0194428 A1 | 10/2003 | Miller et al. | |
| 2003/0194429 A1 | 10/2003 | Miller et al. | |
| 2003/0194430 A1 | 10/2003 | Miller et al. | |
| 2004/0115256 A1 | 6/2004 | MacAllister et al. | |
| 2004/0166153 A1 | 8/2004 | McAllister et al. | |
| 2005/0008690 A1 | 1/2005 | Miller | |
| 2005/0053648 A1 | 3/2005 | Chalmers | |
| 2005/0175687 A1 | 8/2005 | McAllister et al. | |
| 2005/0249807 A1 | 11/2005 | Brown et al. | |
| 2006/0013869 A1 | 1/2006 | Ignatious et al. | |
| 2006/0057201 A1 | 3/2006 | Bonney et al. | |
| 2006/0083784 A1 | 4/2006 | Ignatious et al. | |
| 2006/0177496 A1 | 8/2006 | McAllister et al. | |
| 2009/0148518 A1 | 6/2009 | Brown et al. | |
| 2010/0074947 A1 | 3/2010 | Brown et al. | |

FOREIGN PATENT DOCUMENTS

| | | |
|---|---|---|
| CN | 1489456 A | 4/2004 |
| DE | 3524963 | 1/1987 |
| DE | 3543956 | 6/1987 |
| DE | A-3727894 | 3/1989 |
| EP | 0141397 | 5/1985 |
| EP | 0143524 | 6/1985 |
| EP | 0384642 | 8/1990 |
| FR | 1454013 | 7/1966 |
| FR | 2524311 | 10/1983 |
| GB | 1108629 | 4/1968 |
| GB | 1177587 | 1/1970 |
| GB | 1496737 | 12/1977 |
| GB | 2025270 | 1/1980 |
| GB | 2148235 | 5/1985 |
| GB | 2148814 A | 6/1985 |
| GB | 2148841 | 6/1985 |
| GB | 2172569 | 9/1986 |
| GB | 2187703 | 9/1987 |
| GB | 2283912 | 5/1995 |
| NL | 7610038 | 3/1978 |
| WO | WO 90/12567 | 11/1990 |
| WO | WO 92/13521 | 8/1992 |
| WO | WO 94/09743 | 5/1994 |
| WO | WO 95/13056 | 5/1995 |
| WO | WO 95/16438 | 6/1995 |
| WO | WO 95/17171 | 6/1995 |
| WO | WO 01/08666 A1 | 2/2001 |
| WO | WO 02/060384 A2 | 8/2002 |
| WO | WO 02/060385 A2 | 8/2002 |
| WO | WO 03/086267 | 10/2003 |
| WO | WO 2004/010978 A1 | 2/2004 |
| WO | WO 2004/014304 | 2/2004 |
| WO | WO 2005/009380 A1 | 2/2005 |
| WO | WO 2005/089726 A2 | 9/2005 |

OTHER PUBLICATIONS

"Sweetening the Pill." www.carclo.co.uk, *Engineering*, Sep. 2006.
English language Abstract of DE 3524963.
English language Abstract of DE 3543956.

* cited by examiner

PANELED CAPSULE SHELLS FOR RELEASE OF PHARMACEUTICAL COMPOSITIONS

PRIORITY

This application claims priority to U.S. Provisional Patent Application No. 60/960,787 filed Oct. 15, 2007.

FIELD OF THE INVENTION

This invention relates to capsules for pharmaceutical dosage forms and, more particularly, to capsule shells for use with a linker part and one or more connected sub-units in a multipart dosage form.

BACKGROUND OF THE INVENTION

Various types of pharmaceutical dosage forms are known for oral dosing. Such capsules generally comprise an envelope wall of a pharmaceutically acceptable, e.g. orally ingestible, polymer material such as gelatin, although other materials for capsule walls, e.g. starch and cellulose based polymers are also known. Such capsules generally have soft walls made by forming a film on a capsule former, which is then allowed to dry. Rigid walled capsules made by injection molding are also known; see for example U.S. Pat. No. 4,576,284, U.S. Pat. No. 4,591,475, U.S. Pat. No. 4,655,840, U.S. Pat. No. 4,738,724, U.S. Pat. No. 4,738,817, and U.S. Pat. No. 4,790,881 (all to Warner Lambert). These disclose specific constructions of capsules made of gelatin, starch and other polymers, and methods of making them by injection molding of hydrophilic polymer, e.g., water mixtures. U.S. Pat. No. 4,576,284 specifically discloses such capsules provided with a cap which closes the capsule, which is formed in situ on the filled capsule by molding. U.S. Pat. No. 4,738,724 discloses a wide range of rigid capsule shapes and parts.

Multi-compartment capsules, including those of the type where the compartments have different drug release characteristics or, for example, contain a different pharmacological composition (i.e., drug substance or formulation), are also known; see for example U.S. Pat. No. 4,738,724 (Warner-Lambert), U.S. Pat. No. 5,672,359 (University of Kentucky), U.S. Pat. No. 5,443,461 (Alza Corp.), WO 9516438 (Cortecs Ltd.), WO 9012567 (Helminthology Inst.), DE-A-3727894, BE 900950 (Warner Lambert), FR 2524311, NL 7610038 (Tapanhony NV), FR 28646 (Pluripharm), U.S. Pat. No. 3,228,789 (Glassman), U.S. Pat. No. 3,186,910 (Glassman), WO 05/089726, WO 2004/010978, WO 01/08666, US 2005/0175687, and US 2004/0115256, among others. U.S. Pat. No. 4,738,817, U.S. Pat. No. 3,228,789, and U.S. Pat. No. 3,186,910 each disclose a multicompartment capsule made of a water-plasticized gelatin. Capsules which include a matrix of a solid polymer, in which a drug substance is dispersed, embedded or dissolved as a solid solution are also known. Such matrixes may be formed by an injection molding process. See, for example, WO 02/060385, WO 02/060384.

The content of each of the above-mentioned background references is incorporated herein by way of reference.

See, also for example, WO 01/08666, WO 02/060385, US 2004/0115256, US 2006/0049311, WO 02/060384, US 2003/0068369, US 2004/0166153, WO 04/010978, US 2006/0057201, WO 05/009380, US 2005/0175687, WO 05/089726, US 2005/0249807, U.S. 60/968,383, and U.S. 61/061,275, each of the disclosures of which are incorporated herein by way of reference.

Also, the contents of PCT/EP00/07295 entitled "MULTI-COMPONENT PHARMACEUTICAL DOSAGE FORM" assigned to the assignee of this application is incorporated herein by way of reference.

SUMMARY OF THE INVENTION

In one aspect of the present invention, a capsule shell for connection to a linker in multi-part dosage form includes a generally cylindrical shell member having an interior, a longitudinal axis, an outer surface, a closed end, and an open end. The open end is configured to connect to the linker, and the closed end is generally rounded. One or more panels are positioned adjacent the closed end and circumferentially spaced apart about the axis. Each of the panels is integral with the shell member and is configured to have a thickness thinner than a thickness of an adjacent shell member portion, for preferential dissolution to release drug substance from a shell member interior past the outer surface.

The capsule shell can have a ratio of the panel thickness to the shell member thickness in the range of about 0.2 to about 0.6.

In another aspect of the present invention, an injection molded capsule shell for use as a first part of a multipart dosage form includes a generally cylindrical shell member having an interior, a longitudinal axis, an inner surface, an outer surface, a closed end, and an open end. The open end is configured to connect to a second part of the dosage form, and the closed end is generally rounded. One or more panels are positioned within the rounded closed end and are circumferentially spaced apart about the axis. The panels, which may comprise reliefs or depression in the inner surface, are formed by injection molding together with the shell member, and are configured to have a thickness thinner than a thickness of a circumferentially adjacent shell member portion.

The injection molded capsule shell can have panel thicknesses as thin as about 0.1 mm, with a nominal shell member thickness of about 0.5 mm.

The accompanying drawings, which are incorporated in and constitute a part of this specification, illustrate several exemplary embodiments of the invention and together with the description, serve to explain the principles of the invention.

BRIEF DESCRIPTION OF THE DRAWINGS

The invention will now be described by way of example with reference to.

DESCRIPTION OF THE EMBODIMENTS

Reference will now be made in detail to the present embodiments of the invention, examples of which are illustrated in the accompanying drawings.

Figure 1:
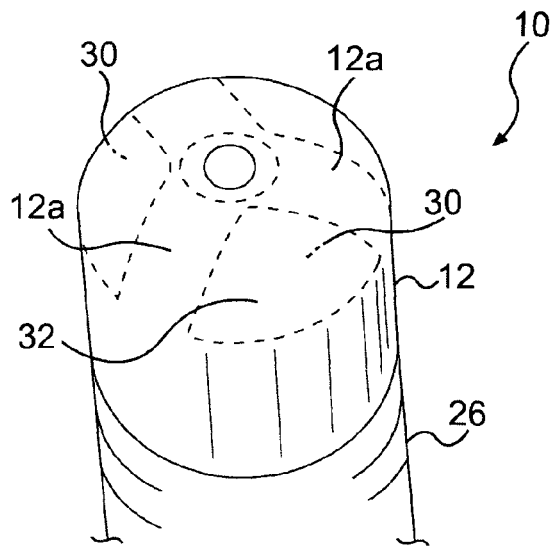
FIG. 1, which is a perspective view of a capsule shell made in accordance with an exemplary aspect of the present invention.

In accordance with one aspect of the present invention, as broadly described and claimed herein, a capsule shell is provided for use in a multipart dosage form for dispensing drug substances at different times and/or places in the gastrointestinal ("GI") tract. As embodied herein and with initial reference to the embodiment depicted in FIGS. 1-3, an exemplary capsule shell designated generally as 10 is intended for use with a linker component or other part of a multipart dosage form.

Figure 3:
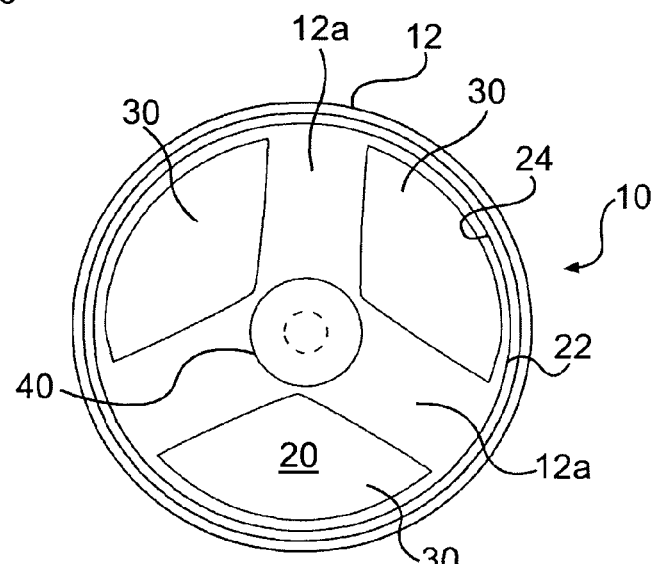
FIG. 3 shows an end view of the capsule shell shown in FIG. 2 along the line 3-3.
Figure 2:
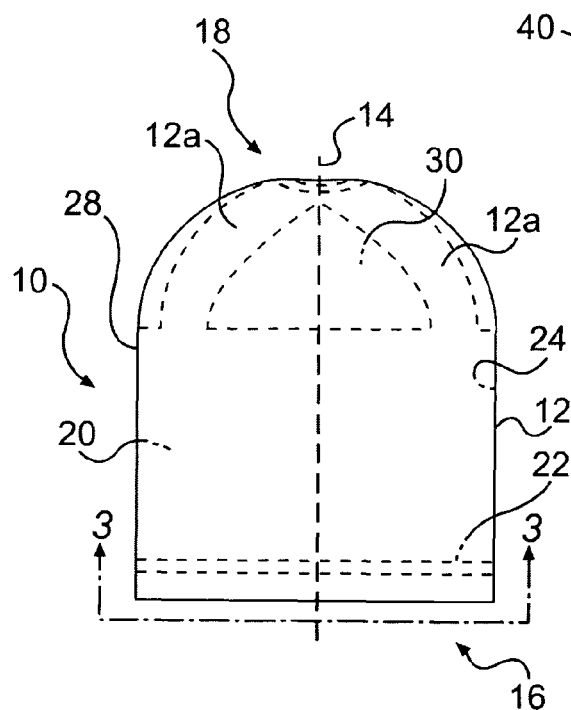
FIG. 2 is a side view of the capsule shell depicted in FIG. 1.

In accordance with the present invention, the capsule shell includes a generally cylindrical shell member having an interior, a longitudinal axis, an outer surface, an open end, and a closed end. As embodied herein, and with continued reference to FIGS. 1-3, capsule shell 10 includes generally cylindrical shell member 12 having longitudinal axis 14 and opposed longitudinal ends 16 and 18. Longitudinal end 16 is "open" to the hollow interior 20 of shell member 12 and is configured for connection to a linker such as linker 26 depicted schematically in FIG. 1. As best seen in FIGS. 2 and 3, snap fit element in the form of a continuous ridge 22 is provided on inner surface 24 of shell member 12. Ridge 22 is engagable with a complementary snap fit element on the linker. For example, if capsule shell 10 used a circumferential ridge as snap fit element 22, the linker 26 may have a complementary circumferential groove (both not shown in FIG. 1). One skilled in the art would understand that continuous ridge 22 could be substituted by a continuous groove and a complementary ridge formed on the linker component. Also, ridge segments could be substituted for continuous ridge 22 and groove segments could be used on the linker as complementary snap fit elements for the ridge segments.

Closed end 18 has a generally rounded configuration and, in combination with the linker, is intended to seal off a substance, such as a drug substance, contained within capsule shell interior 20 until released by dissolution of the panel parts 30 of capsule shell 10 (to be discussed hereinafter) through shell member outer surface 28. See FIG. 2. Outer surface 28 may be configured to have no discontinuities, abrupt edges, or asperities that would hinder swallowing.

Further in accordance with the present invention, the capsule shell includes one or more panels integral with the shell member and positioned adjacent the closed end, the panels being configured to have thicknesses thinner than the thicknesses of adjacent shell member portions. As embodied herein, and with continued reference to FIGS. 1-3, the generally triangular shaped panels 30 are provided in the form of reliefs/depressions in inner shell surface 24 adjacent closed end 18. The top surfaces 32 of panels 30 may be substantially continuous with shell member outer surface 28. The triangular panels 30 are oriented with a vertex extending toward axis 14. This orientation provides the circumferential width of panels 30 decreasing in the longitudinal direction toward the junction of closed end 18 and axis 14.

It may be preferred, for reasons to be explained hereinafter, that panels 30 have an axial length less than the entire shell member length and, more preferably, to be substantially entirely located on inner surface 24 within the rounded portion of shell member end 18. Panels 30 are circumferentially spaced about axis 14 with respective adjacent shell member portions 12a separating the panels. Adjacent shell member portions 12a may provide a more rigid frame or "cage"-like structure for supporting the comparatively thinner panels 30, such as during processing of the capsules and handling by the consumer. Although panels 30 are shown spaced equidistantly in the circumferential direction in FIGS. 1-3, an irregular spacing could be used. One skilled in the art would be able to configure and position such panels given the present disclosure.

Further, and as best seen in FIGS. 2 and 3, capsule shell 10 preferably includes a generally convex protuberance portion 40 located on inner surface 24 at the juncture of closed end 18 and axis 14. Protuberance 40 may be formed using a cold slug well in an inner mold, in an injection molding process. The thickness of portion 40 generally may be greater than the nominal thickness of shell member 12, including adjacent shell portions 12a. Protuberance 40 acts to join or interconnect adjacent shell member portions 12a and may provide more rigidity to the shell member portions surrounding panels 30.

Figure 4:
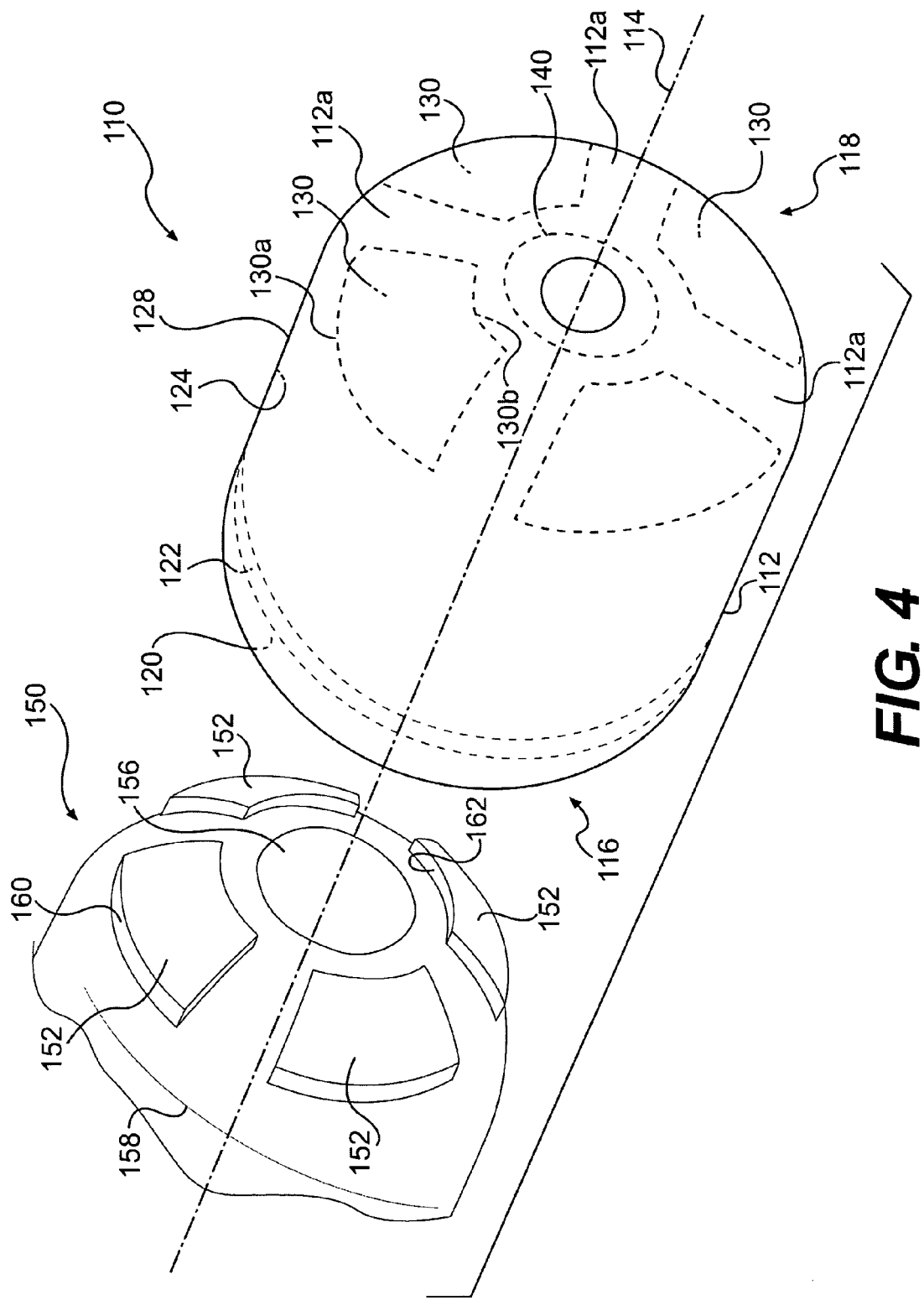
FIG. 4 is a perspective view of a capsule shell made in accordance with another exemplary aspect of the present invention.

FIG. 4 discloses another embodiment of the present invention, specifically the capsule shell designated generally by the number 110. Capsule shell 110 is configured specifically for manufacture by injection molding. For convenience, like parts and features relative to the embodiment in FIGS. 1-3 will be designated by the same numeral (i.e., XX) but with a base 100 (i.e., 1XX).

As shown in FIG. 4, capsule shell 110 includes shell member 112, having interior 120, longitudinal axis 114, open end 116, and rounded closed end 118. Four circumferentially spaced, trapezoidally shaped panels 130 are provided on inner surface 124. The trapezoidally shaped panels 130 are oriented with the minor bases adjacent the juncture of closed end 118 and axis 114, in order to locate all the panels substantially within rounded closed end 18 to allow release of capsule shell 110 from a mold, as will be discussed hereinafter. Panels 130 have curved major and minor base edges to further facilitate release. One skilled in the art would realize from a consideration of FIGS. 1-3 and 4, that a greater or lesser number of individual panels could be provided, as well as shapes different from the triangular and trapezoidal shapes shown in the figures.

Also shown in FIG. 4 is a depiction of a suitable inner mold part 150 for forming capsule shell 110 by injection molding. Mold part 150, which essentially defines inner shell member surface 124, includes raised trapezoidal areas 152 for forming the reliefs/depressions that will comprise panels 130 in capsule shell 110. Importantly, not only the placement, but also the shapes and edge configurations of the raised areas 152 affect the ease with which the molded capsule 110 can be released from mold part 150. That is, raised areas 152 may be configured not only to provide capsule panels with sufficient area for disbursement of the contained substance past shell member outer surface 128 upon dissolution, but also to allow release of the molded capsule shell 110 from mold part 150 along the direction of axis 114. For example, the raised trapezoidal area 152 may be located and configured such that an axial projection of the raised trapezoidal areas fall within an axial projection of the outer diameter 158 of mold part 150. Also, top and bottom edges 160, 162 of raised area 152 may be made parallel to axis 114 to facilitate release of capsule shell 110 along the axial direction. One skilled in the art would understand from the description and drawings herein how to achieve these functions in a specific case.

Still further, and with continued reference to FIG. 4, shell member 112 includes protuberance 140, which may be a generally convex thickened portion (relative to nominal shell thickness) on shell member interior surface 124 at the juncture of closed end 118 and axis 114. As with protuberance 40 in the embodiment shown in FIGS. 1-3, protuberance 140 may provide additional structural rigidity by interconnecting the adjacent shell member portions 112a. Protuberance 140 is provided by capsule molding material filling concave cold slug well 156 in mold inner part 150. It should be understood that for capsules formed by injection molding, the mold material could advantageously be introduced to the mold in the vicinity of well 156, which would help distribute the material in the mold particularly into the relatively thin reliefs/depressions forming panels 130.

Figure 5:
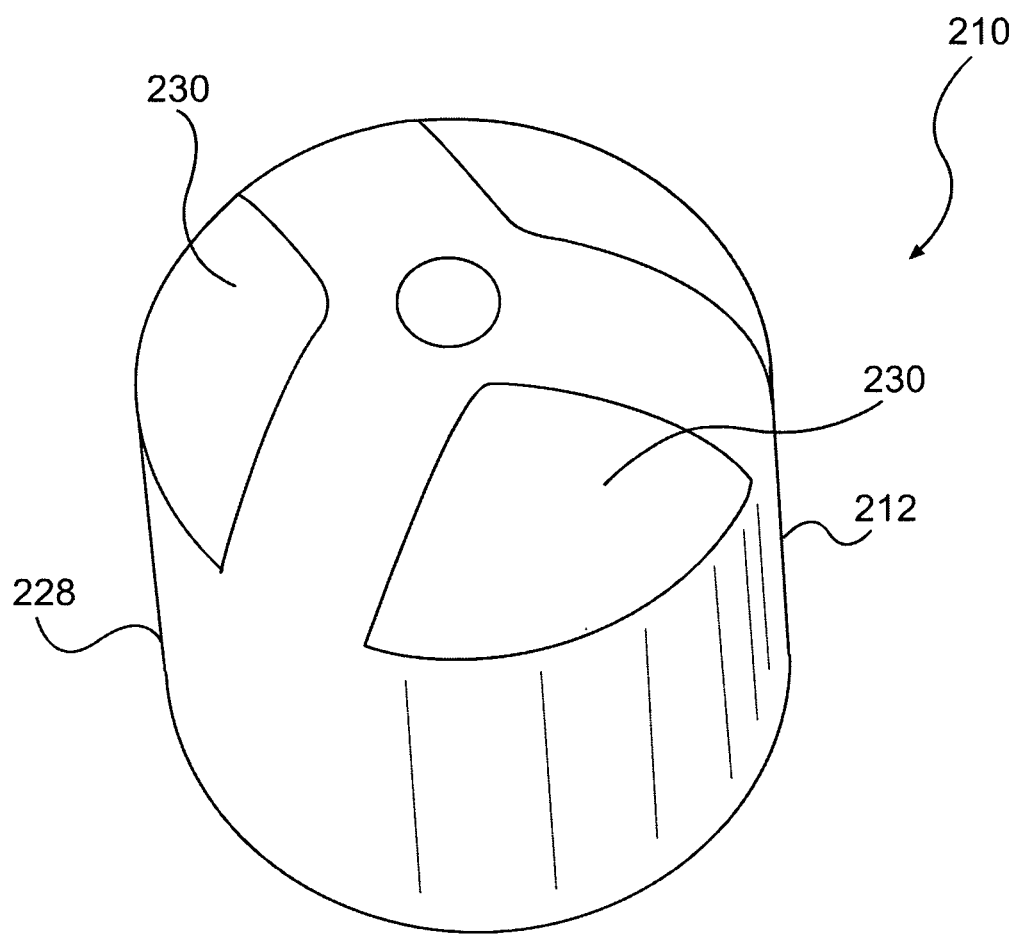
FIG. 5 is a perspective view of a capsule shell made in accordance with yet another exemplary aspect of the present invention.

Still further, capsule shells may be provided in accordance with the present invention by reliefs/depressions/indents in the outer surface of the shell member. For instance, FIG. 5 schematically depicts capsule shell 210 having depressions forming triangular shaped panels 230 in outer surface 228 of shell member 212, in a construction similar to capsule shell 10 in FIGS. 1-3 except for location of the depressions. Different shapes and numbers of panels such as the four trapezoidally shaped panels of FIG. 4 could, of course, be formed by depressions on outer surfaces of the shell members. For such embodiments, an outer mold part (not shown) could be provided with suitably configured and located raised areas on its inner surface that would define the outer shell member surface and thus the indented panels on the molded capsule shell.

Although the capsules of the present invention could be made by the "dip pin" molding process well known to those skilled in the art, it may be preferred to manufacture the capsules by injection molding. Suitable materials for injection molding the capsules of the present invention, including capsule shell 30 of FIGS. 1-3 and capsule shells 110 of FIG. 4 and 210 of FIG. 5, include transitional polymers and may comprise the same or different polymers. A transitional polymer is a polymer that changes shape, form, or structure within a gastro-intestinal environment, e.g., is dispersible, dissolvable, disintegrable, breachable, swellable, partially or completely soluble, fracturable, or otherwise changeable when exposed to stomach pH and/or in intestine pH to thereby expose an interior portion thereof. Suitable polymers for injection molding the capsules include: polyvinyl alcohol (PVA), natural polymers (such as polysaccharides like pullulan, carrageenan, xanthan, chitosan or agar gums), polyethylene glycols (PEG), polyethylene oxides (PEO), mixtures of PEGS and PEOS, hydroxypropylmethylcellulose (HPMC), methylcellulose, hydroxyethylcellulose, hydroxyethyl methylcellulose, hydroxypropylcellulose, methacrylic acid copolymer (such as Eudragit E™, Eudragit L™ and/or Eudragit S™), ammonium methacrylate copolymers (such as Eudragit RL™ and/or Eudragit RS™), carboxymethylcellulose, povidone (polyvinyl pyrrolidone), polyglycolysed glycerides (such as Gelucire 44/14™, Gelucire 50/02™, Gelucire 50/13™ and Gelucire 53/10™), carboxyvinyl polymers (such as Carbopols™), polyoxyethylene-polyoxypropylene copolymers (such as Poloxamer 188™), and acrylic and/or methacrylic acid-based polymers. The Eudragit™ polymers discussed above for example are extrudable and may for example be plasticized with e.g. triethyl citrate, or glyceryl monostearate.

Preferred polymers are orally ingestible polymers and include hydroxypropyl methylcellulose acetate succinate (HPMC-AS), polyvinyl alcohol, hydroxypropyl methyl cellulose, and other cellulose-based polymers. Preferred polymers also include polymer materials which preferentially dissolve or disintegrate at different points in the digestive tract. Such polymers include the known acrylic and/or methacrylic acid-based polymers which are transitional in intestinal fluids, e.g. the Eudragit series of commercially available polymers. Examples of these include Eudragit E™, such as Eudragit E 100™ or Eudragit 4135F™, which preferentially dissolves in the more acid pH of the stomach, or enteric polymers such as Eudragit L™ and/or Eudragit S™ which preferentially dissolve in the more alkaline pH of the intestine, and preferred polymers also include polymers which dissolve slowly, e.g. at a predetermined rate in the digestive tract, such as Eudragit RL™ e.g. Eudragit RL 100™, and/or Eudragit RS™ e.g. Eudragit R100™, and/or blends of such Eudragit™ polymers.

The polymers may include other substances to modify their properties and to adapt them to various applications, including, for example, the following general classes of substances: surfactants, such as Polysorbate 80™, sodium lauryl sulphate, and Polyoxyl 40™ hydrogenated castor oil; absorption enhancers, such as Labrasol™, Transcutol™; glidants, such as stearyl alcohol, talc, magnesium stearate, silicon dioxide, amorphous silicic acid, fumed silica, Simeticone™; plasticizers, such as triethyl citrate, acetyl triethyl citrate, tributyl citrate, acetyl tributyl citrate, glyceryl monostearate, diethyl phthalate, dibutyl phthalate, propylene glycol, triacetin and castor oil; substances for release modification, such as ethyl cellulose and cellulose acetate phthalate; disintegrants, such as sodium starch glycollate, croscarmellose sodium, crospovidone (cross-linked polyvinyl pyrrolodone), coloring agents, flavoring agents and sweetening agents. These materials have appropriate dissolution properties and are capable of forming capsule shell structures having a shell member nominal thickness of about 0.5 millimeters with sufficient rigidity to allow handling, including automatic filling, as well as support for the thinner panels as was discussed previously.

Also, it has been found that these materials can be used to injection mold capsule shells having panel thicknesses as thin as about 0.2-0.3 mm without holes developing during the molding process. It is expected that with further refinements in the injection molding equipment and process, shell members having panels as thin as about 0.1 mm or less would be achieved using the panel configurations disclosed herein and in light of the considerations discussed above.

In this regard, it is further preferred to configure the shell member and panel portions of the capsule shells in accordance with the present invention, including but not limited to capsule shells 10, 110, and 210, to have a ratio of the panel thickness to the adjacent shell member portion thickness in the range of about 0.2 to about 0.6. This range may help ensure controlled, preferential dissolution of the panels at a predetermined time and/or location, such as in the gastrointestinal ("GI") tract while maintaining sufficient rigidity for handling.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. Capsule shell for connection to a linker in a multipart dosage form, the capsule shell comprising:
   a generally cylindrical shell member having an interior, a longitudinal axis, an outer surface, a closed end, and an open end, the open end being configured to connect to the linker, and the closed end being generally rounded; and
   one or more panels adjacent the closed end and circumferentially spaced apart about the axis, each of the panels being integral with the shell member and configured to have a thickness thinner than a thickness of an adjacent shell member portion;
   wherein at least one of the panels is a relief or depression formed in an inner surface of the shell member;

wherein the one or more panels have a length along the axis; and wherein an outer surface of the one or more panels is flush with the outer surface of the shell member along the entire length.

2. The capsule shell as in claim 1, wherein at least one of the panels has a circumferential width that decreasingly tapers in the longitudinal direction toward the closed end.

3. The capsule shell as in claim 1, wherein at least one of the panels extends along only a part of a longitudinal length of the shell member.

4. The capsule shell as in claim 1, having three or more panels.

5. The capsule shell as in claim 1, wherein at least one of the panels is configured to provide preferential dissolution relative to the adjacent shell member portion, to release a substance from the shell member interior past the outer surface.

6. The capsule shell as in claim 1 having a plurality of panels circumferentially spaced equidistantly apart about the axis.

7. The capsule shell as in claim 1, wherein at east one of the panels has a generally trapezoidal shape.

8. The capsule shell as in claim 7, wherein the at least one trapezoidal panel has curved major and minor base edges, and axially tapered opposing side edges.

9. The capsule shell as in claim 1, wherein at least one panel has a generally triangular shape.

10. The capsule shell as in claim 1, wherein the shell member and panels are formed of the same material.

11. The capsule shell as in claim 1, wherein the material is selected from the group consisting of hydroxypropyl cellulose, hydroxypropyl methylcellulose acetate succinate, polyvinyl alcohol, hydroxypropyl methyl cellulose, and acrylic or methacrylic acid-based polymers.

12. The capsule shell as in claim 1, wherein the shell member and panels are formed simultaneously by molding.

13. The capsule shell as in claim 12, wherein the shell member and panels are injection molded.

14. The capsule shell as in claim 13, wherein the shell member and panels are configured for release from a mold along the axial direction.

15. The capsule shell as in claim 1, wherein the shell member further includes a protuberance on an inner shell member surface at the closed end, and wherein the panels terminate adjacent the protuberance.

16. The capsule shell as in claim 1, wherein one or more snap fit elements are provided on an inner shell member surface adjacent the open end, said snap fit elements for engaging complementary snap fit elements on the linker.

17. The capsule shell as in claim 16, wherein the snap fit elements are selected from circumferential grooves, ridges, groove segments, and ridge segments.

18. The capsule shell as in claim 1, wherein at least one of the panels is positioned substantially entirely at the shell rounded end.

19. The capsule shell as in claim 1, wherein a ratio of the panel thickness to the adjacent shell member portion thickness is in a range of about 0.2 to about 0.6.

20. The capsule shell as in claim 1, wherein the shell member and integral panels are formed by injection molding, wherein a thickness of the adjacent shell member portions is about 0.5 mm.

21. The capsule shell as in claim 1, wherein the shell member and integral panels are formed by injection molding, and wherein the thickness of at least one of the panels is about 0.1 mm.

22. The capsule shell as in claim 20, wherein the shell member and integral panels are formed by injection molding, and wherein the thickness of at least one of the panels is about 0.2-0.3 mm.

23. The capsule shell as in claim 20, wherein the shell member and integral panels are formed by injection molding, and wherein the thickness of at least one of the panels is about 0.1 mm.

24. An injection molded capsule shell, the capsule shell comprising:

a generally cylindrical shell member having an interior, a longitudinal axis, an inner surface, an outer surface, a closed end, and an open end, the open end being configured to connect to another part of a dosage form, and the closed end being generally rounded; and one or more panels positioned within the rounded closed end and circumferentially spaced apart about the axis, the panels comprising reliefs or depressions in the inner surface, the panels being formed by injection molding with the shell member and configured to have a thickness thinner than a thickness of a circumferentially adjacent shell member portion;

wherein the one or more panels have a length along the axis; and wherein an outer surface of the or more panels is flush with the outer surface of the shell member along, the entire length.

25. The injection molded capsule shell as in claim 24, wherein the panel thickness is greater than or equal to about 0.1 mm.

26. The injection molded capsule shell as in claim 24, wherein the panels each terminate at a location proximate an entry point of the capsule shell material into the mold cavity.

27. The injection molded capsule shell as in claim 25, wherein the thickness of the shell member is about 0.5 mm.

28. The injection molded capsule shell as in claim 24, further including a protuberance positioned on the inner shell member surface at a juncture of the axis and the closed end, the thickened portion interconnecting adjacent shell member portions.

29. The injection molded capsule shell as in claim 24 wherein the other dosage form part is a linker part.

30. The injection molded capsule shell as in claim 24 having a linker part of the dosage form attached to the open end.

* * * * *

UNITED STATES PATENT AND TRADEMARK OFFICE
CERTIFICATE OF CORRECTION

PATENT NO. : 8,454,992 B2  
APPLICATION NO. : 12/285843  
DATED : June 4, 2013  
INVENTOR(S) : Stephen Mark McAllister It is certified that error appears in the above-identified patent and that said Letters Patent is hereby corrected as shown below:

In the Claims:

Claim 24, col. 8, line 36, "along, the entire" should read --along the entire--.

Signed and Sealed this  
Eighth Day of October, 2013

Teresa Stanek Rea  
*Deputy Director of the United States Patent and Trademark Office*